US012582776B2

(12) United States Patent
Oda et al.

(10) Patent No.: US 12,582,776 B2
(45) Date of Patent: Mar. 24, 2026

(54) SYRINGE WITH PRIMING INDICATOR

(71) Applicant: CAREFUSION 303, INC., San Diego, CA (US)

(72) Inventors: Todd Oda, Torrance, CA (US); George Mansour, Diamond Bar, CA (US); Eugene Mason, La Habra, CA (US)

(73) Assignee: CAREFUSION 303, INC., San Diego, CA (US)

( * ) Notice: Subject to any disclaimer, the term of this patent is extended or adjusted under 35 U.S.C. 154(b) by 1052 days.

(21) Appl. No.: 17/548,946

(22) Filed: Dec. 13, 2021

(65) Prior Publication Data

US 2022/0096753 A1 Mar. 31, 2022

Related U.S. Application Data

(63) Continuation of application No. 16/403,412, filed on May 3, 2019, now Pat. No. 11,229,745.

(51) Int. Cl.
| | |
|---|---|
| *A61M 5/31* | (2006.01) |
| *A61M 25/06* | (2006.01) |
| *A61M 39/10* | (2006.01) |

(52) U.S. Cl.
CPC ...... *A61M 5/3146* (2013.01); *A61M 25/0693* (2013.01); *A61M 2005/3125* (2013.01); *A61M 39/10* (2013.01)

(58) Field of Classification Search
CPC .............. A61M 5/3146; A61M 5/3158; A61M 5/3148; A61M 5/31596; A61M 2005/2026; A61M 25/0693
(Continued)

(56) References Cited

U.S. PATENT DOCUMENTS 9,402,959 B2 8/2016 Schabaach et al.
10,328,211 B2 * 6/2019 Shetty ............... A61M 5/31528
(Continued)

FOREIGN PATENT DOCUMENTS

CN 101219248 A 7/2008
CN 102510762 A 6/2012
(Continued)

OTHER PUBLICATIONS

International Search Report and Written Opinion for Application No. PCT/US2020/031059, dated Jul. 2, 2020, 16 pages.
(Continued)

*Primary Examiner* — Phillip A Gray
(74) *Attorney, Agent, or Firm* — MASCHOFF BRENNAN

(57) ABSTRACT

Syringes are described herein. A syringe includes a syringe body, a first plunger, a biasing member, and a priming indicator. The syringe body defines a syringe cavity, a syringe port, and an indicator window, wherein the syringe port is in fluid communication with the syringe cavity. The first plunger comprises a first plunger shaft extending from the first plunger, the first plunger disposed within the syringe cavity and defining a first chamber in the syringe cavity, wherein the first chamber is in fluid communication with the syringe port. The biasing member couples to the first plunger shaft, wherein the biasing member urges the first plunger from an unprimed position to a primed position toward the syringe port. The priming indicator presents the first indicator portion through the indicator window in the unprimed position and presents the second indicator portion through the indicator window in the primed position.

18 Claims, 13 Drawing Sheets

(58) Field of Classification Search
USPC ......................................................... 604/207
See application file for complete search history.

(56)                    References Cited

U.S. PATENT DOCUMENTS

| | | |
|---|---|---|
| 2002/0004652 A1 | 1/2002 | Asbaghi |
| 2009/0005735 A1 | 1/2009 | Wikner et al. |
| 2012/0172793 A1 | 7/2012 | Cronenberg et al. |
| 2015/0196714 A1 | 7/2015 | Creaturo |
| 2018/0110927 A1 | 4/2018 | Frias Goyenechea et al. |
| 2018/0280622 A1 | 10/2018 | Li et al. |

FOREIGN PATENT DOCUMENTS

| | | |
|---|---|---|
| CN | 109641107 A | 4/2019 |
| EP | 2480276 A1 | 8/2012 |
| GB | 201815825 A | 4/2020 |
| JP | 2013505093 A | 2/2013 |
| JP | 2015181534 A | 10/2015 |
| WO | WO-2015047758 A2 * | 4/2015 ........ A61M 5/31583 |

OTHER PUBLICATIONS

Chinese Office Action for Application No. 202080046121.3, dated Jan. 15, 2024, 21 pages including machine translation.
Japanese Office Action for Application No. 2021-564984, dated Jan. 12, 2024, 6 pages including translation.
Australian Office Action for Application No. 2020268887, dated Sep. 9, 2024, 3 pages.
Canadian Office Action for Application No. 3,138,299, dated Aug. 14, 2023, 3 pages.
Chinese Notification to Grant for Application No. 202080046121.3, dated May 27, 2024, 7 pages including machine translation.

* cited by examiner

SYRINGE WITH PRIMING INDICATOR

CROSS-REFERENCE TO RELATED APPLICATION

This application is a continuation application of U.S. patent application Ser. No. 16/403,412, titled "SYRINGE WITH PRIMING INDICATOR," filed May 3, 2019, issued as U.S. Pat. No. 11,229,745 on Jan. 25, 2022, the entirety of which is incorporated herein by reference.

FIELD OF THE INVENTION

The present disclosure generally relates to medication delivery systems, and, in particular, to syringes.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, a syringe. Certain configurations of IV sets may have extended lengths of tubing, for example, in excess of 6 feet. Additionally, tubing may be primed with saline prior to the infusion of a liquid medication.

In some applications, during the use of IV catheters, saline from the priming process may be delivered to patient before the liquid medication is delivered to the patient.

SUMMARY

In one or more embodiments, a syringe including a syringe body defining a syringe cavity and a syringe port, wherein the syringe port is in fluid communication with the syringe cavity; a medication plunger disposed on a plunger shaft, the medication plunger disposed within the syringe cavity and defining a medication chamber in the syringe cavity, wherein the medication chamber is in fluid communication with the syringe port; a biasing member disposed along a portion of the plunger shaft, wherein the biasing member urges the medication plunger from an unprimed position to a primed position toward the syringe port; a priming mechanism coupled to the biasing member, the priming mechanism comprising a through hole disposed within a priming shaft; and a retention mechanism releasably coupling the priming shaft to the syringe body, wherein the retention mechanism prevents the biasing member from advancing the medication plunger in an engaged position and permits the biasing member to advance the medication plunger in a released position.

In one or more embodiments, a medication delivery system includes a syringe, having a syringe body defining a syringe cavity and a syringe port, wherein the syringe port is in fluid communication with the syringe cavity; a medication plunger disposed on a plunger shaft, the medication plunger disposed within the syringe cavity and defining a medication chamber in the syringe cavity, wherein the medication chamber is in fluid communication with the syringe port; a biasing member disposed along a portion of the plunger shaft, wherein the biasing member urges the medication plunger from an unprimed position to a primed position toward the syringe port; a priming mechanism coupled to the biasing member, the priming mechanism comprising a through hole disposed within a priming shaft; and a retention mechanism releasably coupling the priming shaft to the syringe body, wherein the retention mechanism prevents the biasing member from advancing the medication plunger in an engaged position and permits the biasing member to advance the medication plunger in a released position; and a tubing in fluid communication with the syringe port and a catheter.

In one or more embodiments, a method to deliver medication via the medication delivery system is disclosed that comprises releasing the retention mechanism; advancing the medication plunger disposed within the syringe via the biasing member; and directing medication from the medication chamber into the tubing, wherein the tubing extends from the syringe to the catheter and defines a tubing volume.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The disclosed syringe incorporates a priming indicator to signal when a medication delivery system is primed with medical fluids. The priming indicator can be coupled to the priming mechanism. By indicating the priming status via the priming indicator, a clinician can be informed when priming is complete.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to the administration of medical fluid using the disclosed syringe, it is to be understood that this description is only an example of usage and does not limit the scope of the claims. Various aspects of the disclosed syringe may be used in any application where it is desirable to indicate the status of a syringe.

The disclosed syringe overcomes several challenges discovered with respect to certain conventional syringes. One challenge with certain conventional syringes is that syringes may deliver excess medical fluid, such as saline, to patients. Further, conventional syringes may not indicate if priming is in process. Because excess medical fluid may delay the delivery of medical fluids, alter dosage of medication, and may not be tolerated by fluid restricted patients, such as premature babies the use conventional syringes is undesirable.

Therefore, in accordance with the present disclosure, it is advantageous to provide a syringe as described herein that simplifies the administration of medical fluids during priming and eliminates or substantially reduces delivering excess medical fluid to a patient. The disclosed syringe provides a priming indicator that provides a status to a clinician while minimizing excess fluid delivered to a patient.

An example of a syringe that indicates priming status and prevents delivery of excess medical fluid is now described.

Figure 1:
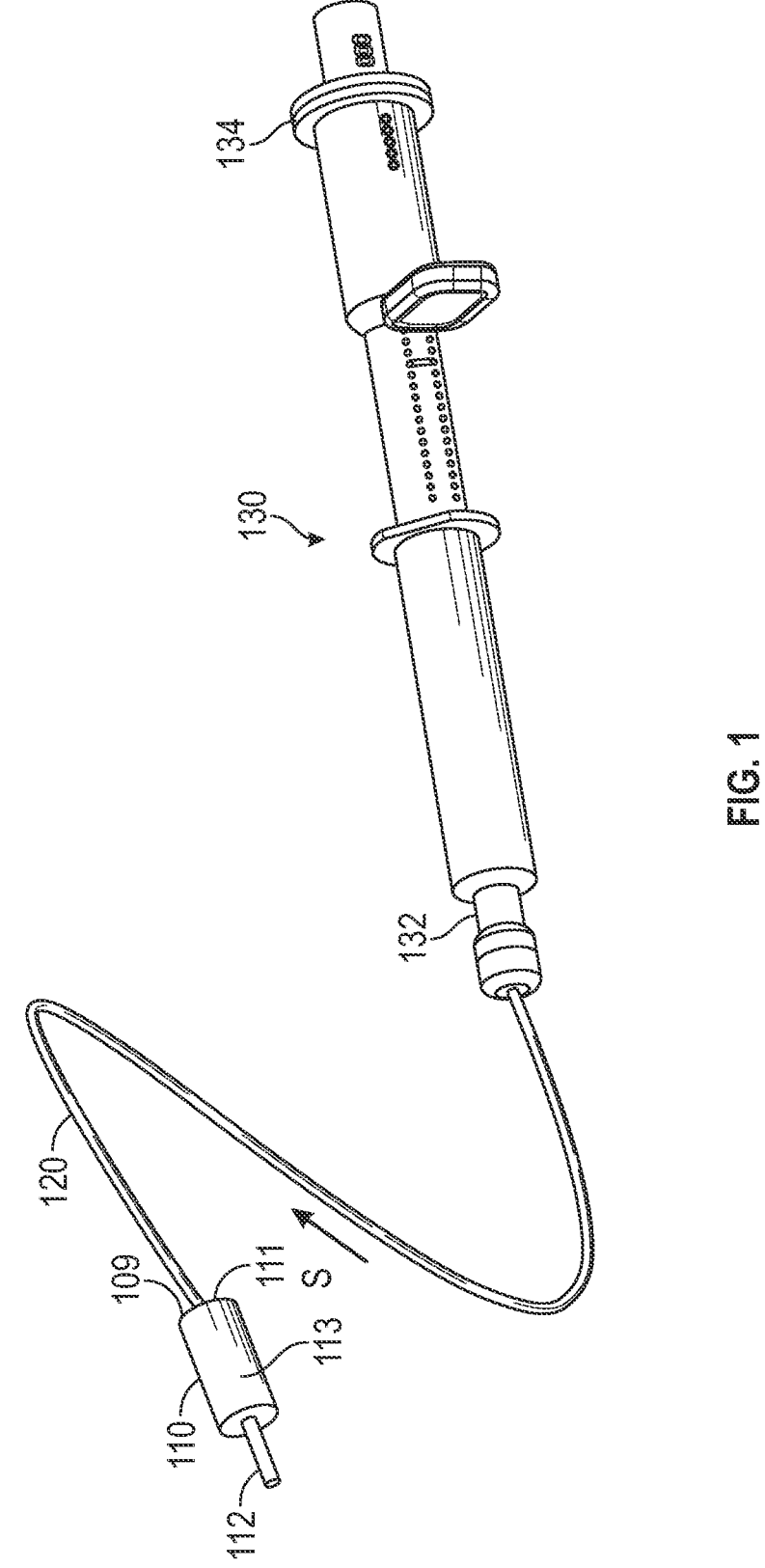
FIG. 1 is a perspective view of a medication delivery system, in accordance with various aspects of the present disclosure.

FIG. 1 is a perspective view of a medication delivery system 100, in accordance with various aspects of the present disclosure. In the illustrated example, the medication delivery system 100 delivers medication from the syringe 130 to the patient via a catheter 112 without delivering excess fluid, such as saline, used to prime the medication delivery system 100.

In some embodiments, a medication flow path within a dual lumen tubing 120 can be primed with saline to remove any air or trapped gasses within the medication flow path of the dual lumen tubing 120. Saline can be advanced from a proximal end 132 of the syringe 130, through the medication flow path of the dual lumen tubing 120 and to the valve 110.

The saline from the medication flow path of the dual lumen tubing 120 can be received by the medication flow path 111 of the valve 110. In a priming configuration, a valve element 113 can prevent saline from the medication flow path 111 from entering the patient catheter 112 and can instead direct the saline toward the return flow path 109 of the valve 110 to allow primed saline to be returned to the syringe 130 via the return flow path of the dual lumen tubing 120.

Figure 2:
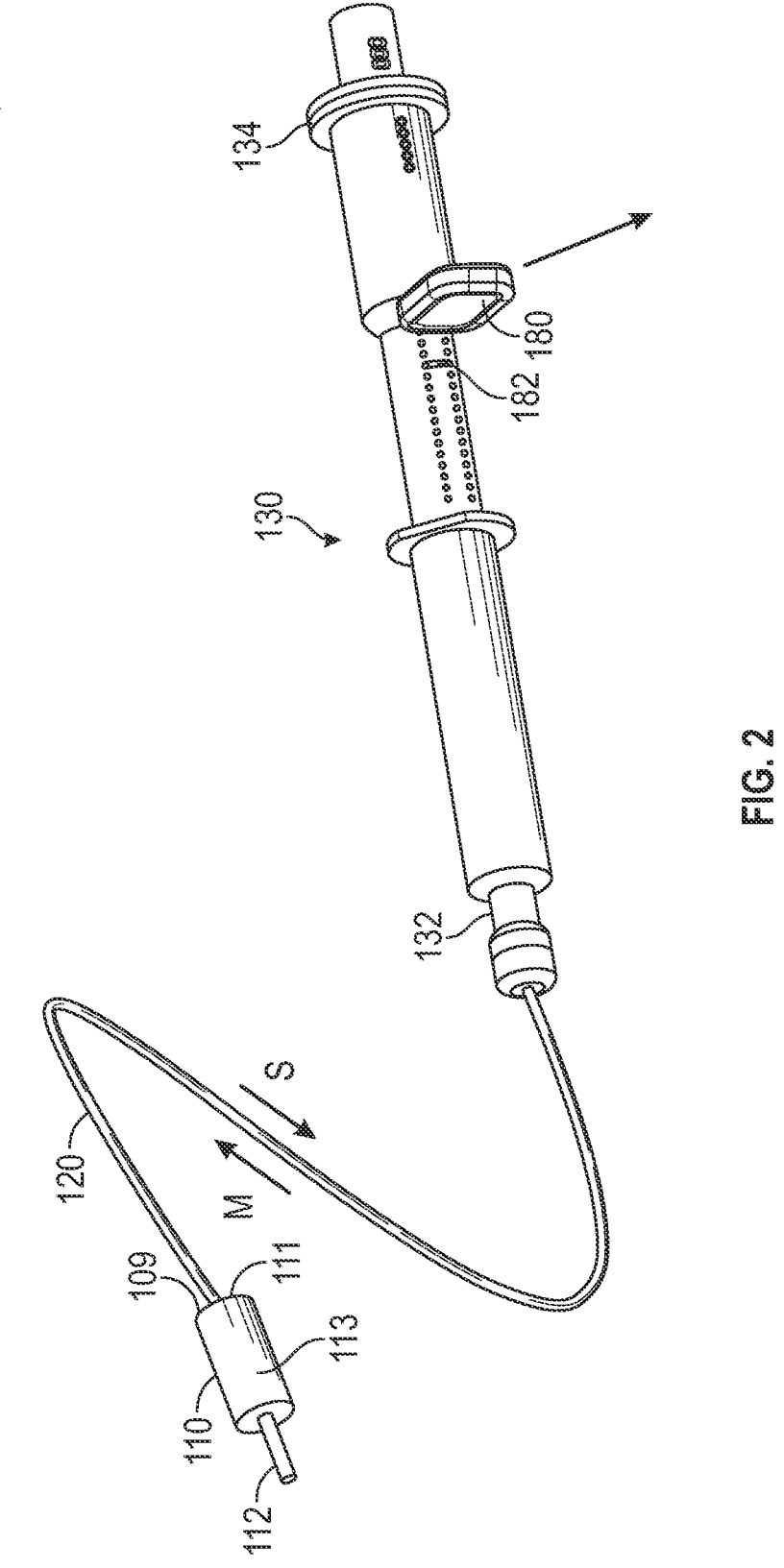
FIG. 2 is a perspective view of the medication delivery system of FIG. 1 with the priming trigger removed, in accordance with various aspects of the present disclosure.

FIG. 2 is a perspective view of the medication delivery system 100 of FIG. 1 with the priming trigger 180 removed, in accordance with various aspects of the present disclosure. In the illustrated example, the syringe 130 advances medication within the medication flow path of the dual lumen tubing 120 to prime the medication flow path of the dual lumen tubing 120. Advantageously, by priming the medication flow path with medication, the medication can be delivered to the patient via the catheter 112 proximal to the patient with less delay and without delivering the saline used to prime the medication flow path of the dual lumen tubing 120.

To introduce medication into the medication flow path of the dual lumen tubing 120, the medication plunger within the syringe 130 can be advanced or otherwise displaced to introduce a volume of medication into the medication flow path of the dual lumen tubing 120. Optionally, the medication plunger of the syringe 130 can be configured to be advanced or displaced a desired amount to dispense a volume of medication into the medication flow path of the dual lumen tubing 120 that is equivalent to the volume of the medication flow path of the dual lumen tubing 120. In other words, medication plunger of the syringe 130 can be advanced to fill the volume of the medication flow path of the dual lumen tubing 120 up to the valve element 113 to prime the medication for administration via the catheter 112.

In some embodiments, the priming of medication into the medication flow path of the dual lumen tubing 120 can be automated or otherwise simplified. For example, the medication plunger can be biased to be advanced to introduce medication into the medication flow path of the dual lumen tubing 120. The biasing member of the priming mechanism within the syringe 130 can be released by removing the priming trigger 180. By removing the priming trigger 180, the biasing member can advance the medication plunger to prime the medication within the medication delivery system 100. Optionally, the priming travel of the medication plunger can be stopped or limited by a priming stop 182. By limiting the travel of the medication plunger during priming, a desired volume of medication can be introduced into the medication flow path of the dual lumen tubing 120, for example, sufficient medication volume to fill the medication flow path of the dual lumen tubing 120.

As illustrated, as the medication is introduced into the medication flow path of the dual lumen tubing 120, the saline previously primed through the dual lumen tubing 120 is displaced. The displaced saline is directed by the valve element 113 through the return flow path 109 of the valve 110 and into the return flow path of the dual lumen tubing 120.

Medical fluid from the return flow path of the dual lumen tubing 120 can be returned into the syringe 130. Returned medical fluid such as saline can be introduced into a return or saline chamber of the syringe 130.

Figure 3:
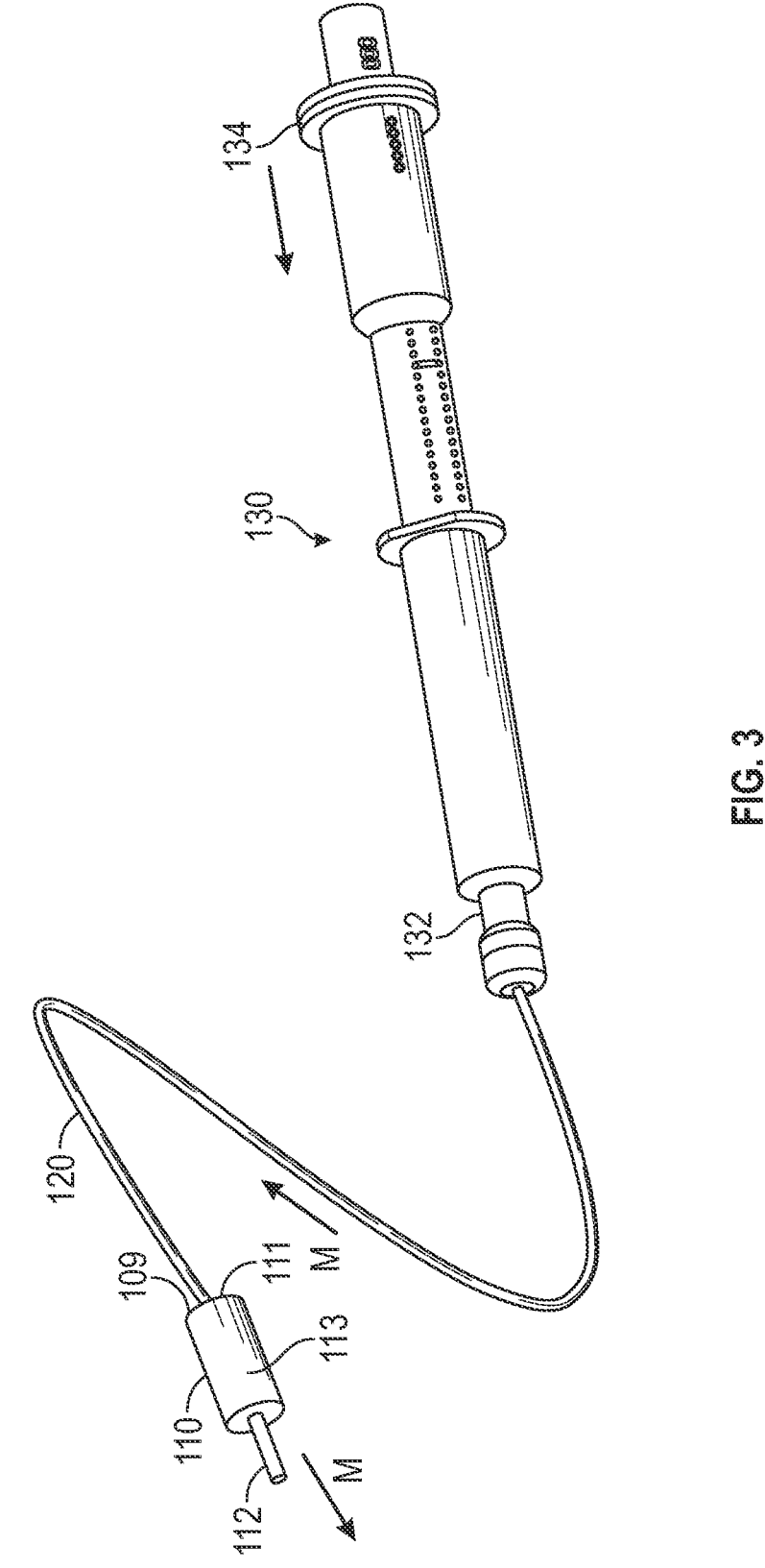
FIG. 3 is a perspective view of the medication delivery system of FIG. 1 with the syringe actuated, in accordance with various aspects of the present disclosure.

FIG. 3 is a perspective view of the medication delivery system 100 of FIG. 1 with the syringe 130 actuated, in accordance with various aspects of the present disclosure. In the illustrated example, the syringe 130 is actuated to dispense medication to the patient through the catheter 112.

As illustrated, the distal end 134 of the syringe 130 can be advanced toward the proximal end 132 of the syringe 130 to actuate the medication plunger within the syringe 130. By actuating the syringe 130, the medication plunger can be advanced to deliver medication from the syringe 130 into the medication flow path of the dual lumen tubing 120. In some embodiments, the syringe 130 can be actuated by a syringe pump to control the flow of medication to the patient.

During operation, the valve 110 is actuated to permit the flow of medication from the medication flow path 111 of the valve 110 to the patient via the catheter 112. In some embodiments, the valve element 113 is actuated to permit fluid communication between the medication flow path 111 and the catheter 112 to allow medication to flow to the patient. Optionally, the valve 110 can be located proximal to the patient to minimize the length of the catheter 112, reduce the amount of saline administered to the patient, and reduce the delivery time for the medication.

Figure 4:
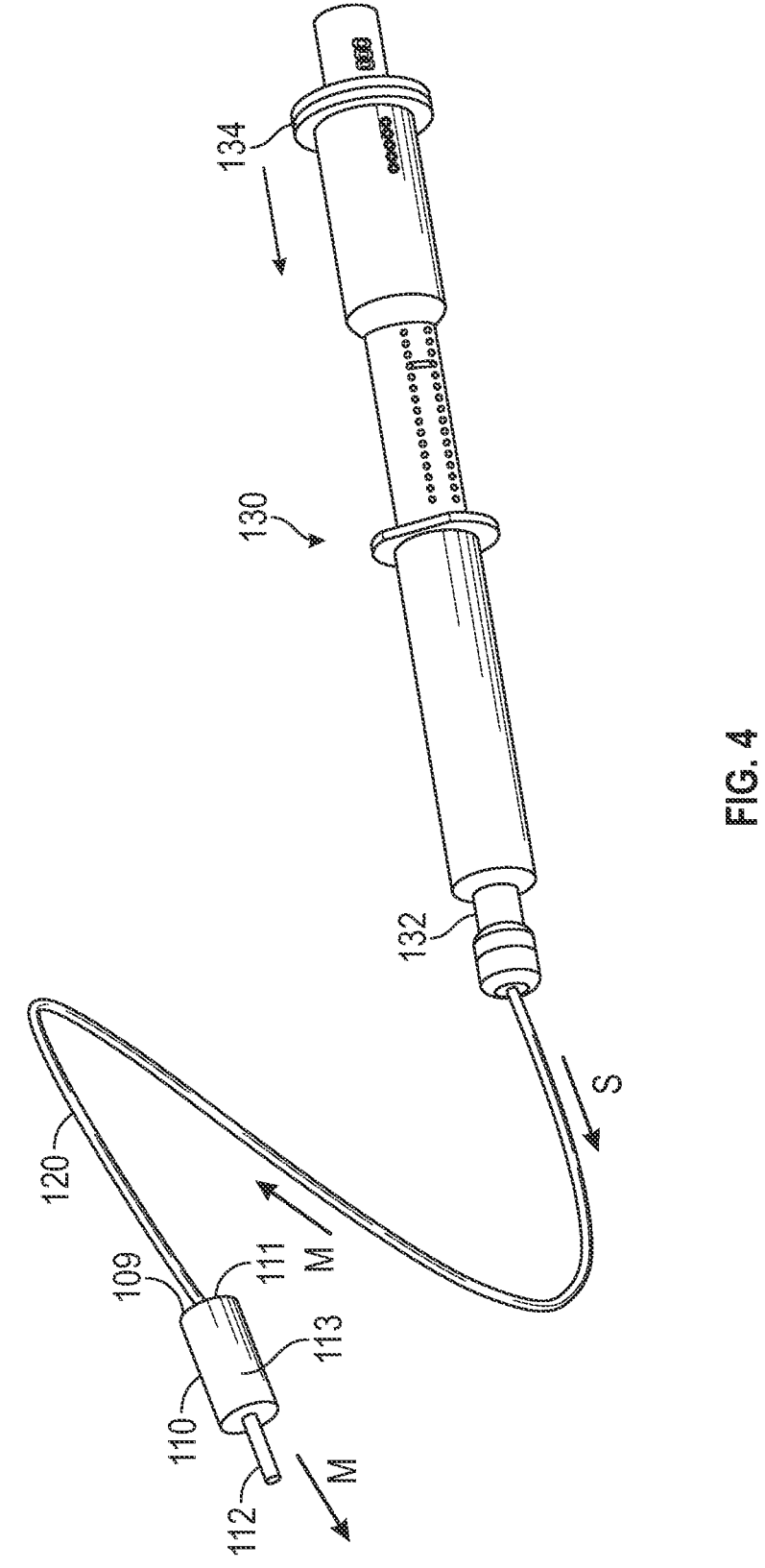
FIG. 4 is a perspective view of the medication delivery system of FIG. 1 with the syringe actuated, in accordance with various aspects of the present disclosure.

FIG. 4 is a perspective view of the medication delivery system 100 of FIG. 1 with the syringe 130 actuated, in accordance with various aspects of the present disclosure. In the illustrated example, the syringe 130 advances saline through the medication flow path of the dual lumen tubing 120 to advance the remaining medication to the patient via the catheter 112.

As illustrated, after the medication is expelled from the syringe 130, medication may remain in the volume of the medication flow path of the dual lumen tubing 120. To ensure that the medication is fully delivered to the patient, the syringe 130 can be utilized to administer a saline "push" to continue to advance the medication through the medication flow path of the dual lumen tubing 120 after the medication within the syringe 130 is exhausted. Optionally, saline can be administered through the medication flow path until the medication is fully administered to the patient.

Figure 5:
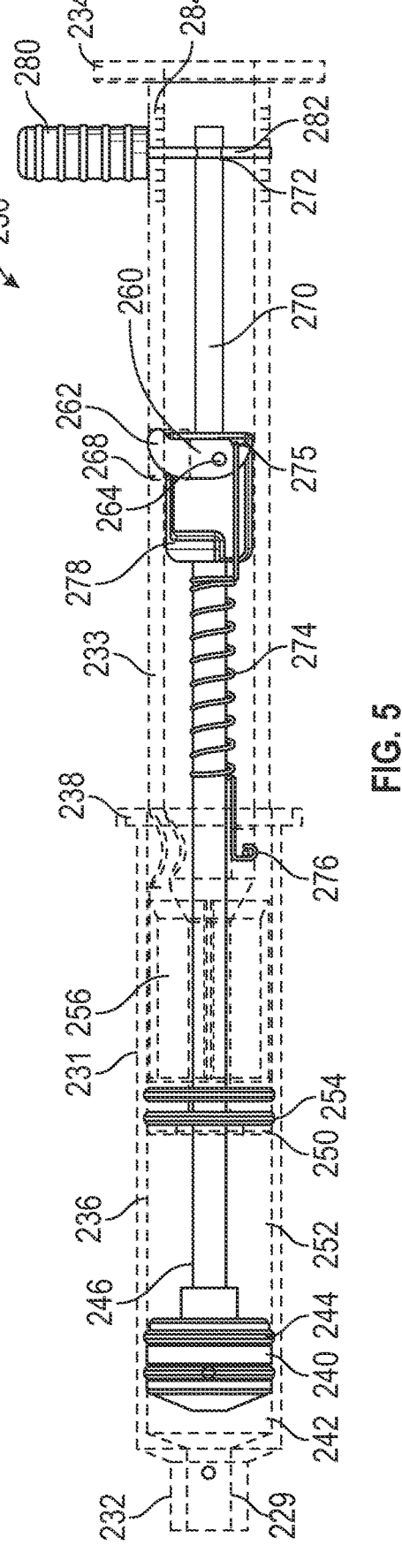
FIG. 5 is an elevation view of a syringe with the syringe body hidden, in accordance with various aspects of the present disclosure.

FIG. 5 is an elevation view of a syringe 230 with the syringe body hidden, in accordance with various aspects of the present disclosure. In the figures, similar features may be referred to with similar reference numerals. In the depicted example, the syringe 230 can be utilized to dispense medication and/or saline through a tubing coupled to the syringe port 229 of the syringe 230. As illustrated, the syringe 230 can receive, store, and/or dispense medication and/or saline in chambers defined therein.

As illustrated, the proximal syringe portion 231 of the syringe 230 can store medical fluids such as medication and saline in a syringe cavity 236. In the illustrated embodiment, the medication plunger 240 is movable within the syringe cavity 236 to define a medication chamber 242 within the proximal syringe portion 231. Optionally, the volume of the medication chamber 242 is defined by the position of the medication plunger 240 relative to the proximal end 232 of the syringe 230. In the depicted example, the medication chamber 242 can store medication.

In some embodiments, the medication chamber 242 is in fluid communication with the syringe port 229 of the syringe 230. Optionally, the medication plunger 240 can include one or more seals 244 to seal against the walls of the syringe cavity 236 to prevent unintended fluid migration or mixing.

Further, the medication plunger 240 can be moved by the medication plunger shaft 246. In some embodiments, the medication plunger 240 can be drawn distally to expand the medication chamber 242 and draw in more medication or medical fluid through the syringe port 229. In some embodiments, the medication plunger 240 can be advanced proximally to contract the medication chamber 242 and expel medication or medical fluid from the medication chamber 242 through the syringe port 229.

In the illustrated embodiment, the saline plunger 250 is movable within the syringe cavity 236 to define a saline chamber 252 within the proximal syringe portion 231. In some embodiments, the saline plunger 250 and the medication plunger 240 cooperatively define the saline chamber 252 within the syringe cavity 236. Optionally, the volume of the saline chamber 252 is defined by the position of the medication plunger 240 and the saline plunger 250. In the depicted example, the saline chamber 252 can store saline or other medical fluids.

Optionally, the saline plunger 250 can include one or more seals 254 to seal against the walls of the syringe cavity 236 to prevent unintended fluid migration or mixing.

Further, the saline plunger 250 can be moved by the saline plunger shaft 256. In some embodiments, the saline plunger 250 can be drawn distally to expand the saline chamber 252 and draw in more saline or medical fluid. In some embodiments, the saline plunger 250 can be advanced proximally to contract the saline chamber 252 and expel saline or medical fluid from the saline chamber 252.

As previously described, during the administration of medication to patients, for example, fluid restricted patients, medication can be dispensed from the medication chamber 242 and then saline can be dispensed from the saline chamber 252 to advance the medication remaining in the tubing.

In the depicted example, medication can be dispensed from the syringe 230 by advancing the medication plunger 240 within the syringe cavity 236. As a result, medication can be delivered from the syringe 230 through the syringe port 229.

In some embodiments, the syringe 230 can include a priming mechanism or actuation mechanism 270 to automate, control, or otherwise simplify advancement of the medication plunger 240 to facilitate the priming of medication into an IV tubing. Optionally, the actuation mechanism 270 can be configured to introduce a sufficient volume of medication from the medication chamber 242 into the IV tubing to fully fill or prime the IV line prior to administration of the medication to the patient.

In the illustrated embodiment, the actuation mechanism 270 can utilize a biasing member such as a tension spring 274 to advance the medication plunger 240 within the syringe cavity 236.

Optionally, the tension spring 274 can be coupled to the proximal syringe portion 231 at the proximal end 276 of the tension spring 274 and coupled to the actuation mechanism 270 at the distal end 275 of the tension spring 274. In some embodiments, the actuation mechanism 270 extends from, or is generally coupled to the medication plunger shaft 246. Further, the tension spring 274 can be disposed around the medication plunger shaft 246.

As illustrated, the tension spring 274 can be preloaded or biased to facilitate advancement of the medication plunger 240 upon release or activation of the tension spring 274. In the depicted example, the tension spring 274 can be extended or biased from a resting length to an elongated tensioned length. In some embodiments, a biasing member can be compressed from a resting length to a shortened compressed length.

As illustrated, the tension spring 274 can be preloaded or elongated by retracting the actuation mechanism 270, which extends the tension spring 274. In some embodiments, the actuation mechanism 270 can be locked or retained in place, preventing the medication plunger 240 from being advanced prior to priming by a retention mechanism. In the illustrated embodiment, the retention mechanism includes a priming trigger 280 with a shaft 282 that extends through the distal syringe portion 233 and through the through hole 272 of the actuation mechanism 270, releasably coupling the actuation mechanism 270 to the distal syringe portion 233. The priming trigger 280 can extend through slot 284 of the distal syringe portion 233.

Optionally, the tension applied to the tension spring 274 can be adjusted by altering the position of the actuation mechanism 270 relative to the distal syringe portion 233 and inserting the priming trigger 280 through a slot 284 aligned with the through hole 272 of the actuation mechanism 270.

Figure 6:
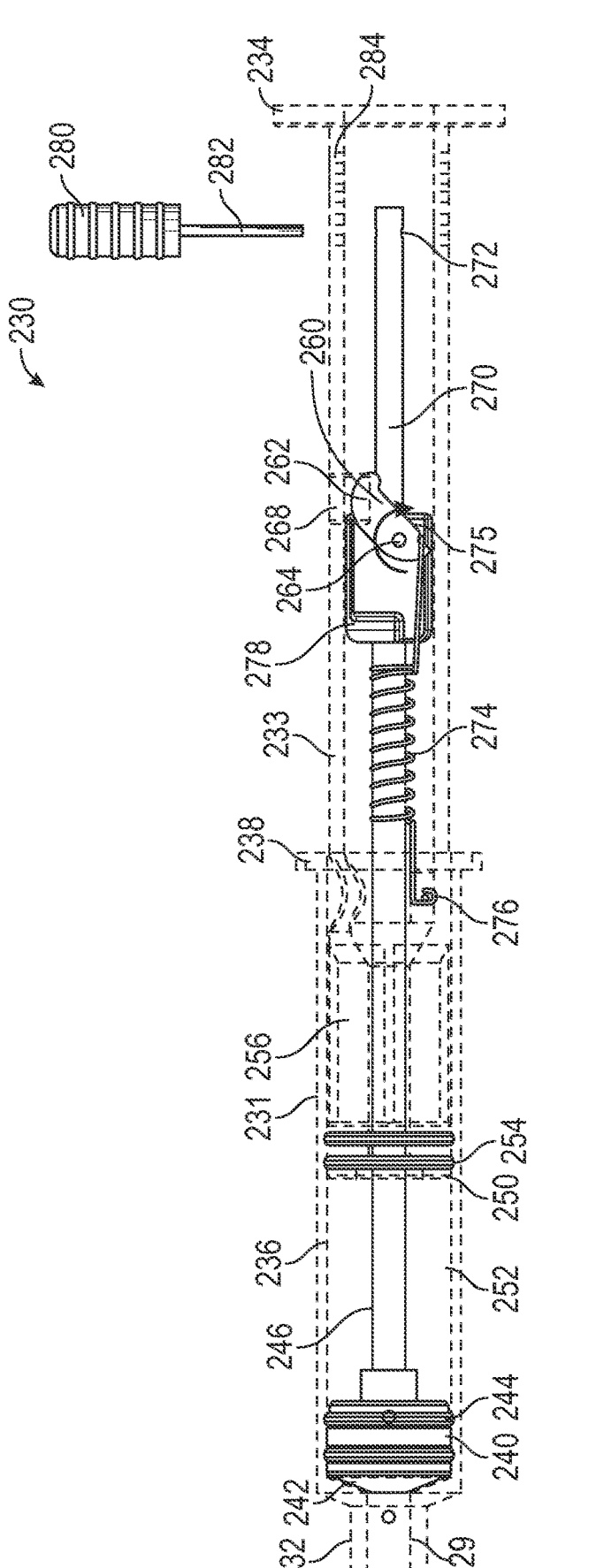
FIG. 6 is an elevation view of the syringe of FIG. 5 with the syringe body hidden and the priming trigger removed, in accordance with various aspects of the present disclosure.

FIG. 6 is an elevation view of the syringe 230 of FIG. 5 with the syringe body hidden and the priming trigger 280 removed, in accordance with various aspects of the present disclosure. As illustrated, the priming mechanism of the syringe 230 can be activated by removing the priming trigger 280 from the syringe 230.

By removing the priming trigger 280, the tension spring 274 is allowed to contract to advance the medication plunger shaft 246 and in turn, the medication plunger 240. By advancing the medication plunger 240, medication within the medication chamber 242 can advance through the IV tubing and prime the IV tubing. As described herein, the medication plunger 240 can be advanced by a desired or predetermined amount corresponding to the IV tubing volume during the priming process.

Figure 7:
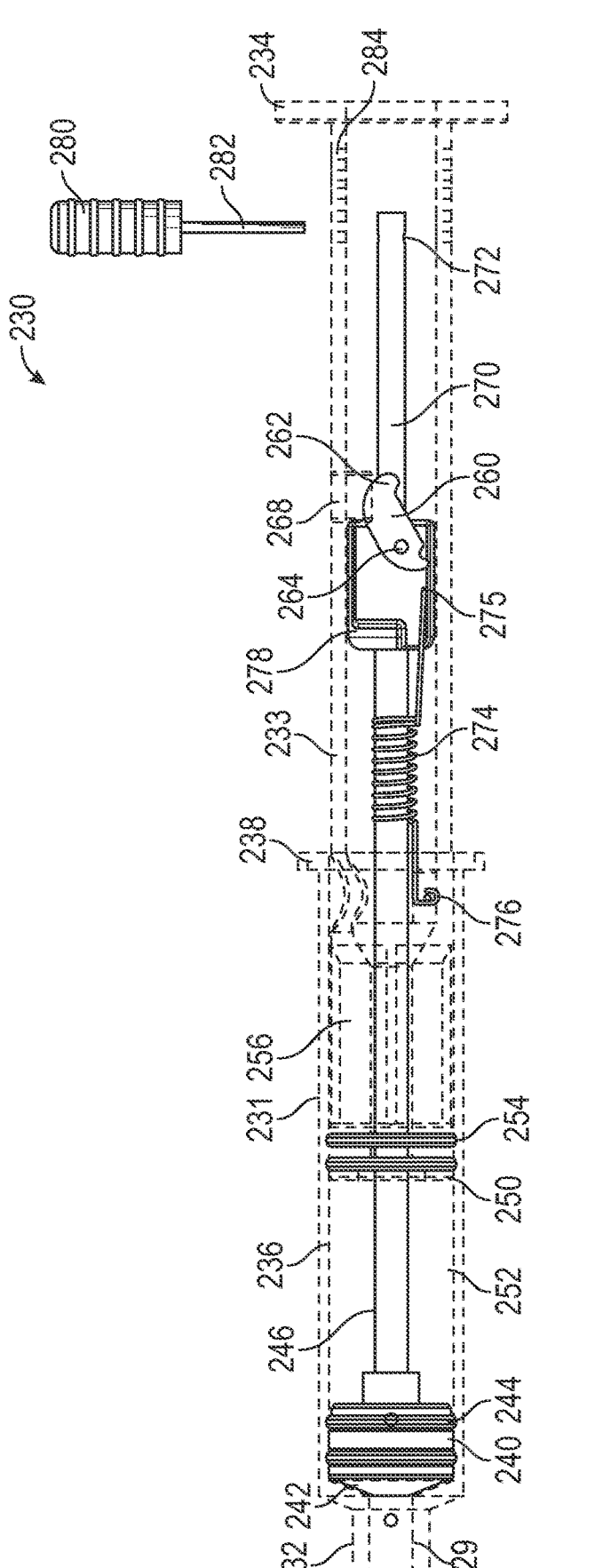
FIG. 7 is an elevation view of the syringe of FIG. 5 with the syringe body hidden and the priming mechanism actuated, in accordance with various aspects of the present disclosure.

FIG. 7 is an elevation view of the syringe 230 of FIG. 5 with the syringe body hidden and the priming mechanism actuated, in accordance with various aspects of the present disclosure. In the illustrated embodiment, the medication plunger 240 can be further actuated to administer any remaining medication in the medication chamber 242 into the IV tubing and to the patient. In some embodiments, the medication plunger shaft 246 can be actuated to advance the medication plunger 240. For example, the distal end 234 of the distal syringe portion 233 can be advanced toward the proximal end 232 to advance the medication plunger 240. In some embodiments, the extensions 238 of the proximal syringe portion 231 can allow a clinician or a syringe pump to advance the distal syringe portion 233 relative to the proximal syringe portion 231.

Figure 8:
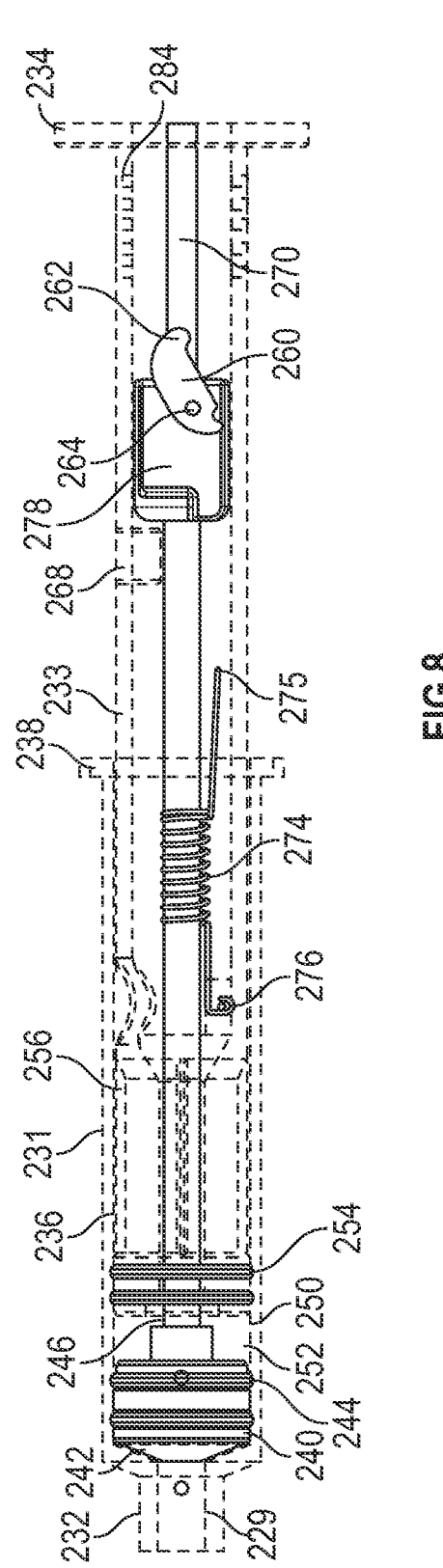
FIG. 8 is an elevation view of the syringe of FIG. 5 with the syringe body hidden and the syringe actuated, in accordance with various aspects of the present disclosure.

FIG. 8 is an elevation view of the syringe 230 of FIG. 5 with the syringe body hidden and the syringe actuated, in accordance with various aspects of the present disclosure. In the illustrated embodiment, the saline plunger 250 can be actuated to administer saline from the saline chamber 252 into the IV tubing to "push" or deliver any remaining medication in the IV tubing to the patient. In some embodiments, the saline plunger shaft 256 can be actuated to advance the saline plunger 250. In some embodiments, the same actuation method for the medication plunger 240 can be utilized for actuating the saline plunger 250.

For example, the distal end 234 of the distal syringe portion 233 can be advanced toward the proximal end 232 to advance the saline plunger 250. In some embodiments, the extensions 238 of the proximal syringe portion 231 can allow a clinician or a syringe pump to advance the distal syringe portion 233 relative to the proximal syringe portion 231.

In some embodiments, saline from the saline chamber 252 can be advanced through or around the medication chamber 242 to exit the syringe 230 via the syringe port 229.

Figure 9:
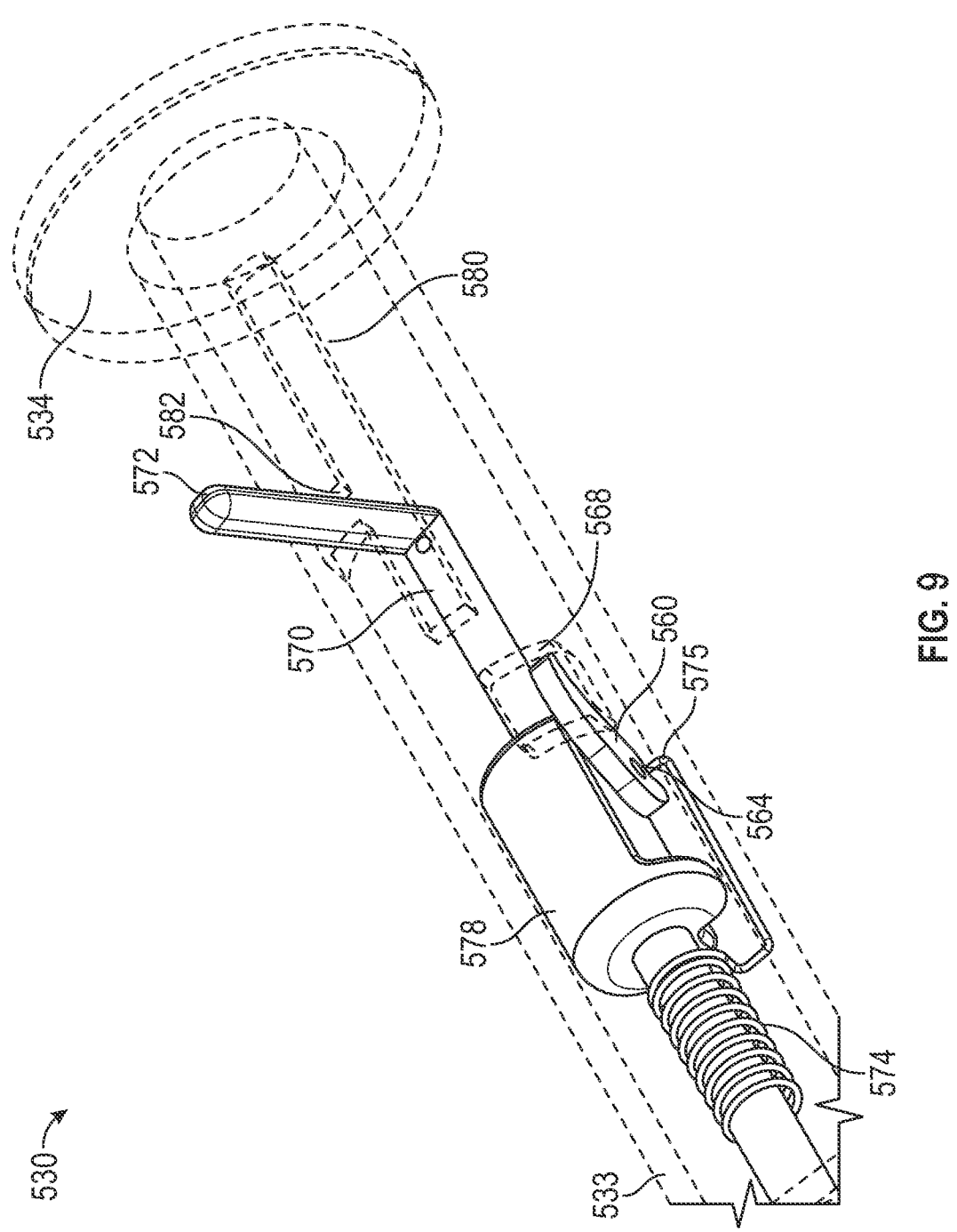
FIG. 9 is a perspective view of an actuation lever of a syringe with the syringe body hidden, in accordance with various aspects of the present disclosure.

FIG. 9 is a perspective view of an actuation lever 572 of a syringe 530 with the syringe body hidden, in accordance with various aspects of the present disclosure. In the illustrated embodiment, the syringe 530 includes an actuation lever 572 to control the energizing and activation of the priming mechanism of the syringe 530.

Similar to syringe 230, in the illustrated embodiment, the actuation mechanism 570 can utilize a biasing member such as a tension spring 574 to advance the medication plunger within the syringe 530. In the depicted example, the tension spring 574 can be coupled to the actuation mechanism 570 at the distal end of the tension spring 574.

In the depicted example, the actuation lever 572 provides an interface to preload or bias the tension spring 574. As illustrated, the actuation lever 572 is coupled to the actuation mechanism 570 and the actuation body 578. Therefore, the actuation lever 572 can be retracted distally within the priming slot 580 to extend or bias the tension spring 574.

Optionally, the actuation mechanism 570 can be locked to prevent the medication plunger from being advanced prior to priming. In the illustrated embodiment, the actuation mechanism 570 is retained by rotating the actuation lever 572 into the retention slot 582. By rotating the actuation lever 572 into the retention slot 582, the proximal edge of the of the retention slot 582 prevents the actuation lever 572, and in turn the actuation mechanism 570 from advancing proximally and dispensing medication. In the illustrated embodiment, the retention slot 582 is generally perpendicular to the priming slot 580.

In some embodiments, the amount of tension applied to the tension spring 574 can be adjusted by including multiple retention slots 582. The actuation lever 572 may be rotated into one of multiple retention slots 582 to adjust the preload exerted upon the tension spring 574.

Figure 10:
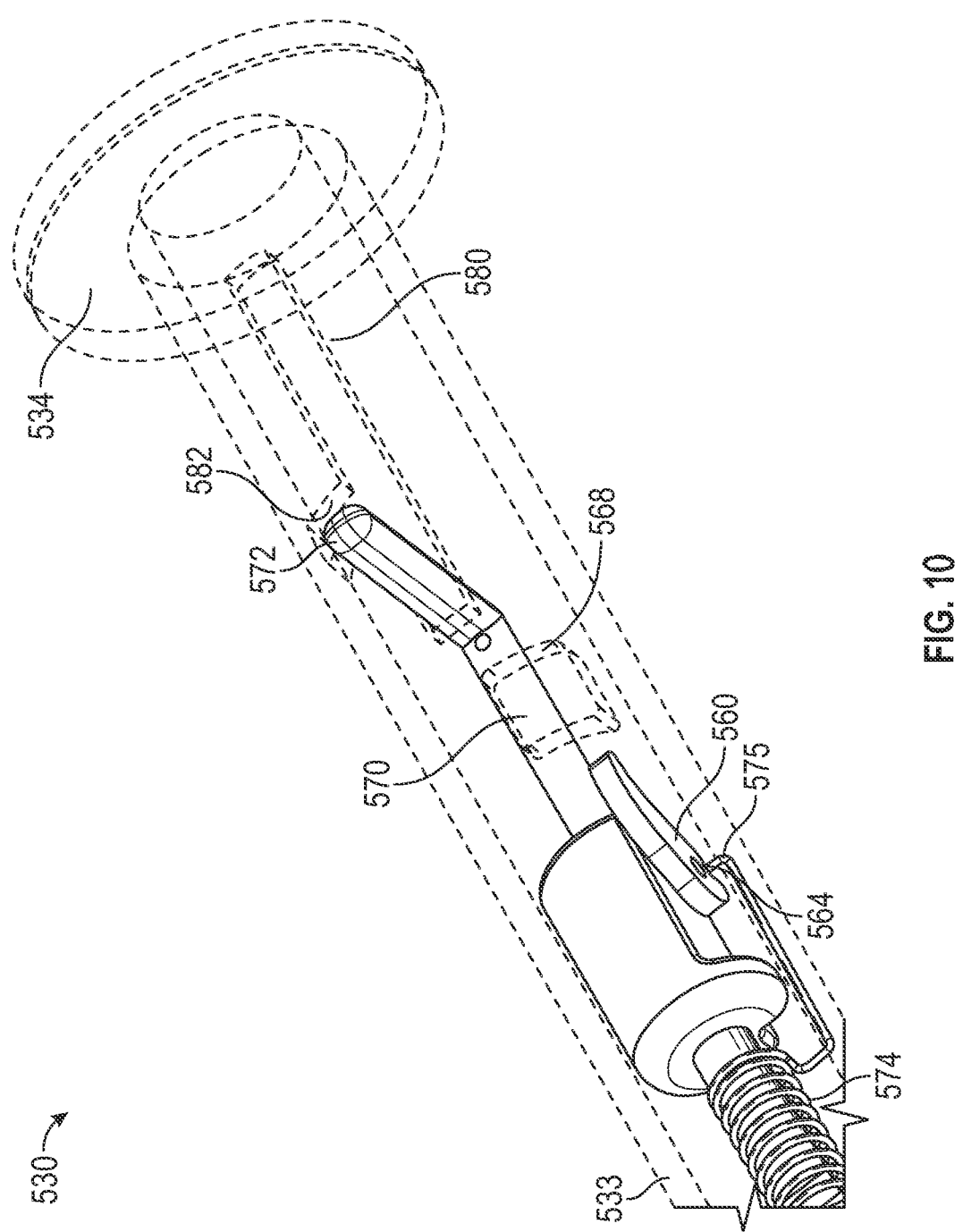
FIG. 10 is a perspective view of the syringe of FIG. 9 with the syringe body hidden and the actuation lever in a released position.

FIG. 10 is a perspective view of the syringe 530 of FIG. 9 with the syringe body hidden and the actuation lever 572 in a released position. As illustrated, the priming mechanism of the syringe 530 can be activated by rotating the actuation lever 572 out of the retention slot 582 and into the priming slot 580. By rotating the actuation lever 572 into the priming slot 580, the tension spring 574 is allowed to advance the medication plunger to prime the IV tubing.

Optionally, the displacement of the medication plunger during priming may be limited by adjusting the length of the priming slot 580. The proximal edge of the priming slot 580 creates a barrier preventing the actuation lever 572 from advancing proximally further than desired, limiting the advancement of the medication plunger. The position of the proximal edge of the priming slot 580, and therefore the fluid displacement during priming, can be adjusted as desired.

Figure 11:
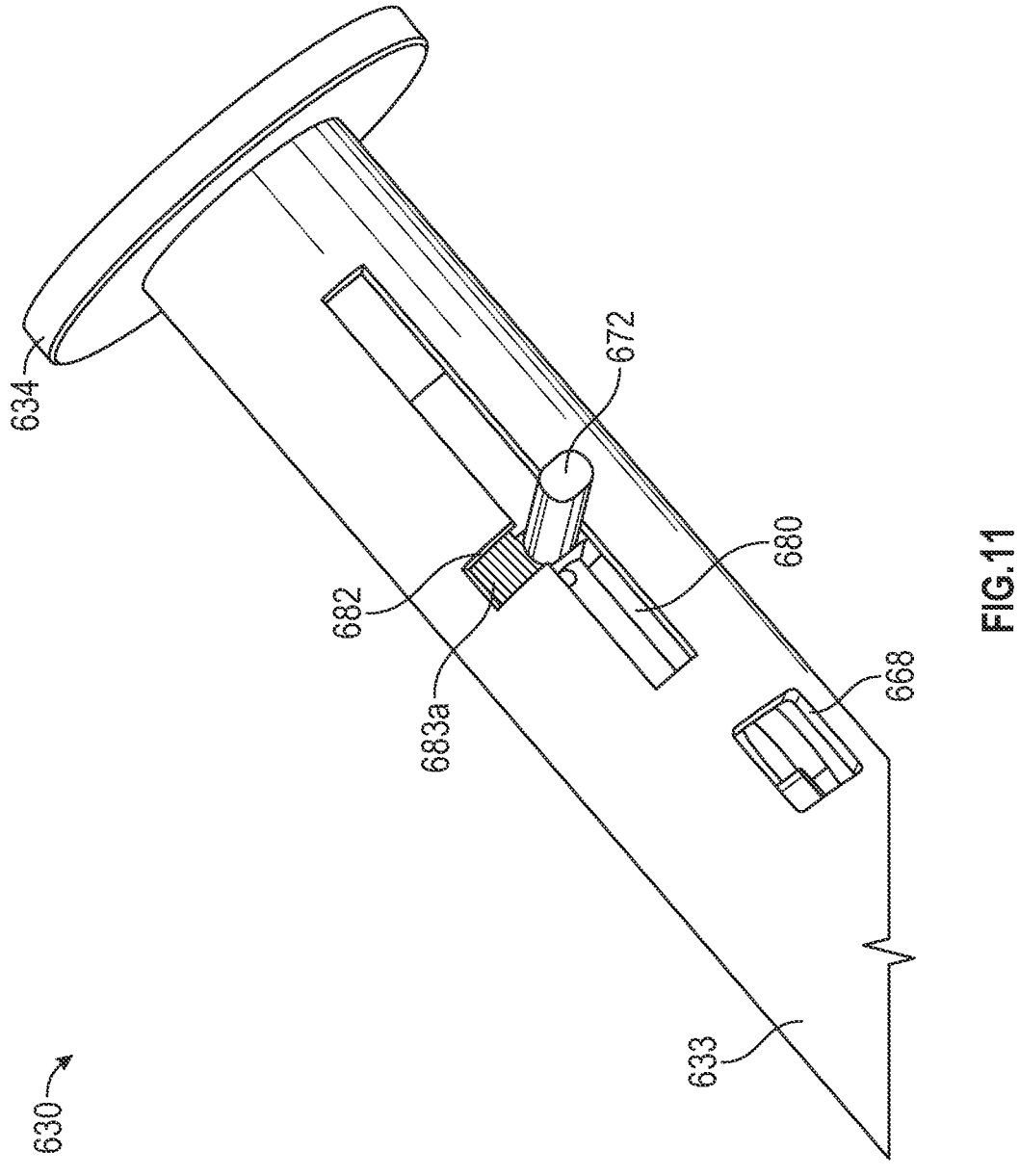
FIG. 11 is a perspective view of a syringe with an unprimed indicator, in accordance with various aspects of the present disclosure.

FIG. 11 is a perspective view of a syringe 630 with an unprimed indicator 683*a*, in accordance with various aspects of the present disclosure. In the illustrated embodiments, the syringe 630 can include a priming indicator configured to signal to a clinician if priming is in process or if priming has been completed.

In the depicted example, the priming indicator can be used with any priming mechanism described herein, including, but not limited to the actuation mechanism 570 described herein. In the illustrated embodiment, the priming indicator can present an unprimed indicator 683*a* when the priming mechanism is in an unprimed position or if priming is in process, and a primed indicator 683*b* when the priming mechanism when the priming mechanism is in a primed position. In some applications, the priming indicator can indicate to a clinician if the priming mechanism is malfunctioning, for example if the priming indicator reflects a status different than the expected status of the priming mechanism.

In some embodiments, the unprimed indicator 683*a* and the primed indicator 683*b* can provide visual signals such as colors, patterns, or words. For example, the unprimed indicator 683*a* can present a red color and the primed indicator 683*b* can present a green color. Optionally, the unprimed indicator 683*a* and the primed indicator 683*b* can present audible or tactile signals, such as mechanism to create clicks or pops, or various textures on the surface of the indicator.

In the depicted example, the priming indicator can be coupled to move with the actuation lever 672 or other portions of the actuation mechanism to reflect the status of the actuation mechanism or priming mechanism. For example, when the actuation lever 672 is in a retained position, the priming mechanism has not been activated and the biasing member within the syringe 630 cannot advance the medication plunger. Prior to activation of the priming mechanism, the unprimed indicator 683*a* may be hidden by the distal syringe portion 633.

During operation, the actuation lever 672 may be rotated to a released position to initiate priming and allow the biasing member to advance the medication plunger. After rotating the actuation lever 672 into the priming slot 680, the unprimed indicator 683*a* can be presented in the retention slot 682, also functioning as an indicator window. Therefore, the indicator window can present unprimed indicator 683*a* when priming begins.

Figure 12:
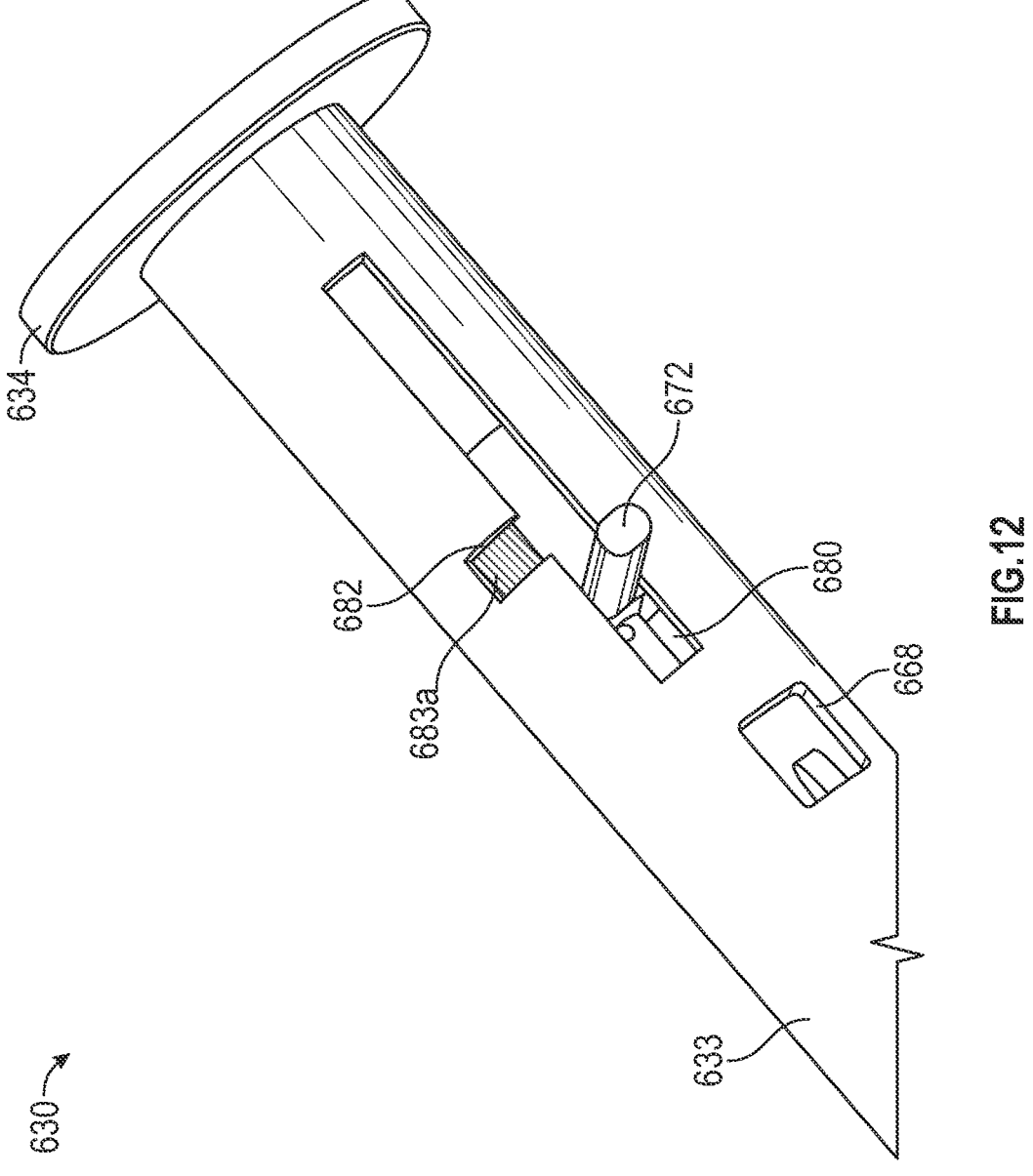
FIG. 12 is a perspective view of the syringe of FIG. 11, in accordance with various aspects of the present disclosure.

FIG. 12 is a perspective view of the syringe 630 of FIG. 11, in accordance with various aspects of the present disclosure. As illustrated, as priming is in process and the medication plunger is advancing, the actuation lever 672 can move proximally toward the proximal edge of the priming slot 680. In the depicted example, the unprimed indicator 683*a* can be configured to be presented in the indicator window. In some embodiments, the length of the unprimed indicator 683*a* can correspond to the travel of the priming mechanism or the length of the priming slot 680 and may therefore present the unprimed indicator 683*a* until the actuation lever 672 has traveled to the end of the priming slot 680.

Figure 13:
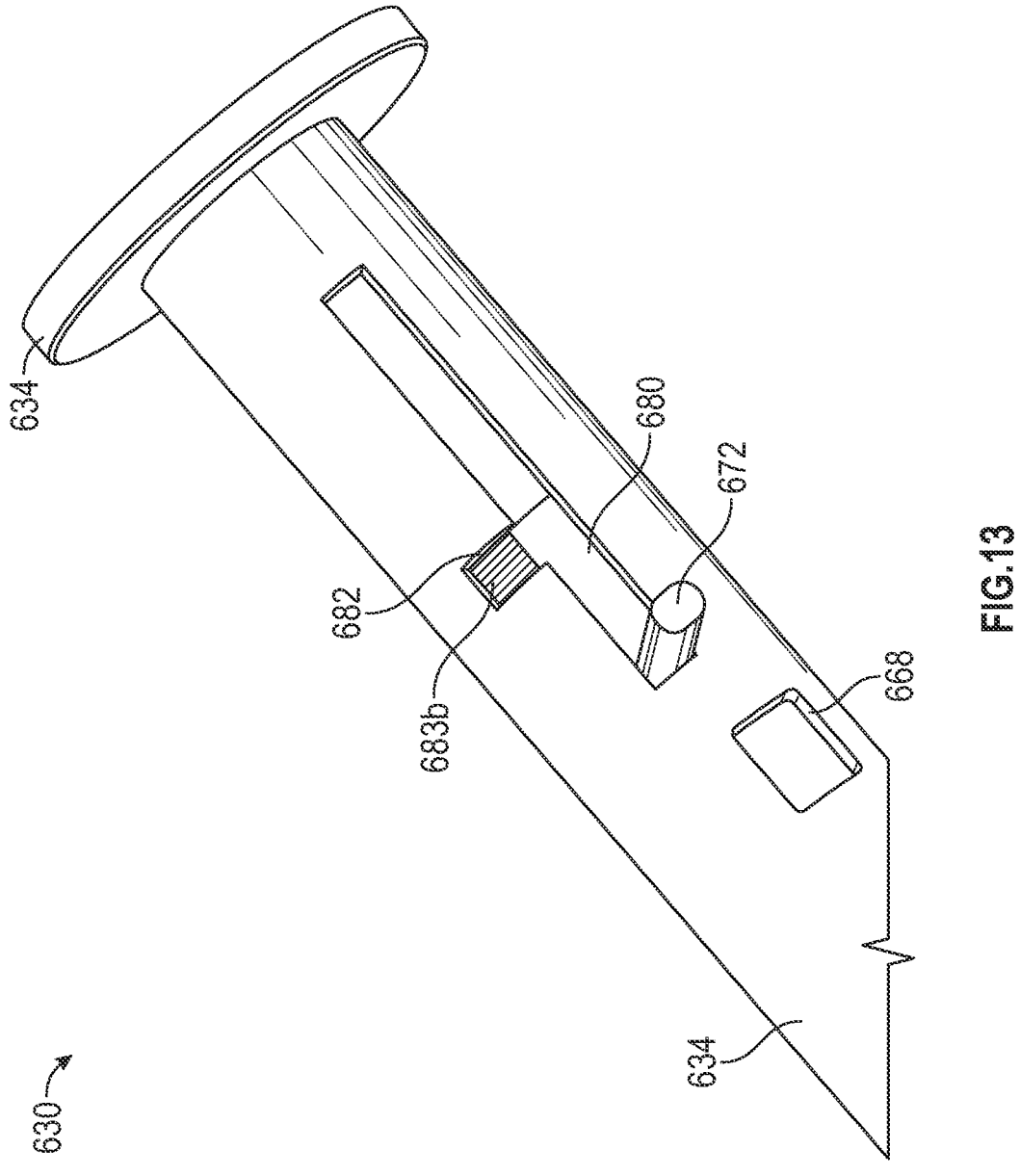
FIG. 13 is a perspective view of the syringe of FIG. 11 with a primed indicator, in accordance with various aspects of the present disclosure.

FIG. 13 is a perspective view of the syringe 630 of FIG. 11 with a primed indicator 683*b*, in accordance with various aspects of the present disclosure. As illustrated, as the priming process is completed, the actuation lever 672 may rest against the proximal edge of the priming slot 680. In the depicted example, the primed indicator 683*b* can be presented via the indicator window to signal to a clinician that the IV tubing is primed with medication. In some embodiments, the primed indicator 683*b* can be positioned to correspond with the end of the travel of the priming mechanism or the end of the priming slot to allow the primed indicator 683*b* to be presented when the actuation lever 672 has traveled to the end of the priming slot 680.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A syringe, comprising:
a syringe body defining a syringe cavity and a syringe port, wherein the syringe port is in fluid communication with the syringe cavity;
a medication plunger disposed on a plunger shaft, the medication plunger disposed within the syringe cavity and defining a medication chamber in the syringe cavity, wherein the medication chamber is in fluid communication with the syringe port;
a biasing member disposed along a portion of the plunger shaft, wherein the biasing member urges the medication plunger from an unprimed position to a primed position toward the syringe port;
a priming mechanism coupled to the biasing member, the priming mechanism comprising a through hole disposed within a priming shaft;
a retention mechanism releasably coupling the priming shaft to the syringe body, wherein the retention mechanism prevents the biasing member from advancing the medication plunger in an engaged position and permits the biasing member to advance the medication plunger in a released position; and
a saline plunger disposed on the plunger shaft, the saline plunger disposed within the syringe cavity and defining a saline chamber in the syringe cavity.

2. The syringe of claim 1, the retention mechanism comprising:
a priming slot formed in the syringe body; and
a priming trigger configured to be releasably coupled to the priming shaft.

3. The syringe of claim 2, the priming trigger comprising:
a trigger shaft configured to extend through the priming slot and to be received by the through hole of the priming shaft, wherein the priming trigger prevents the biasing member from advancing the medication plunger when the trigger shaft is coupled to the priming shaft and permits the biasing member to advance the medication plunger when the trigger shaft is removed from the through hole of the priming shaft.

4. The syringe of claim 1, wherein the medication plunger comprises a seal configured to seal against an inner wall of the syringe cavity.

5. The syringe of claim 1, wherein the medication plunger and the saline plunger cooperatively define the saline chamber within the syringe cavity.

6. The syringe of claim 1, wherein a volume of the saline chamber is defined by a position of the medication plunger and a position of the saline plunger.

7. The syringe of claim 1, wherein the saline plunger comprises a seal configured to seal against an inner wall of the syringe cavity.

8. The syringe of claim 1, further comprising a saline plunger shaft slidably disposed on the plunger shaft, the saline plunger shaft coupled to the saline plunger.

9. The syringe of claim 8, wherein the saline plunger is configured to be drawn away from the syringe port to expand the saline chamber and to be advanced towards the syringe port to contract the saline chamber.

10. The syringe of claim 1, wherein the medication plunger is configured to be advanced toward the syringe port to dispense medication from the medication chamber, and wherein the saline plunger is configured to be advanced toward the syringe port to dispense saline from the saline chamber.

11. The syringe of claim 1, wherein the biasing member is a tension spring coupled between a proximal syringe portion and the priming mechanism.

12. The syringe of claim 11, wherein the biasing member is disposed around the plunger shaft.

13. A medication delivery system, comprising:
a syringe, comprising:
a syringe body defining a syringe cavity and a syringe port, wherein the syringe port is in fluid communication with the syringe cavity;
a medication plunger disposed on a plunger shaft, the medication plunger disposed within the syringe cavity and defining a medication chamber in the syringe cavity, wherein the medication chamber is in fluid communication with the syringe port;
a biasing member disposed along a portion of the plunger shaft, wherein the biasing member urges the medication plunger from an unprimed position to a primed position toward the syringe port;
a priming mechanism coupled to the biasing member, the priming mechanism comprising a through hole disposed within a priming shaft; and
a retention mechanism releasably coupling the priming shaft to the syringe body, wherein the retention mechanism prevents the biasing member from advancing the medication plunger in an engaged position and permits the biasing member to advance the medication plunger in a released position, the retention mechanism comprising:
a priming slot formed in the syringe body; and
a priming trigger configured to be releasably coupled to the priming shaft; and
a tubing in fluid communication with the syringe port and a catheter.

14. The medication delivery system of claim 13, wherein a displacement of the medication plunger from the unprimed position to the primed position is equal to a volume of the tubing between the syringe port and the catheter.

15. The medication delivery system of claim 13, the priming trigger comprising:
a trigger shaft configured to extend through the priming slot and to be received by the through hole of the priming shaft, wherein the priming trigger prevents the biasing member from advancing the medication plunger when the trigger shaft is coupled to the priming shaft and permits the biasing member to advance the medication plunger when the trigger shaft is removed from the through hole of the priming shaft.

16. A method to deliver medication via the medication delivery system of claim 13, the method comprising:

releasing the retention mechanism;

advancing the medication plunger disposed within the syringe via the biasing member; and directing medication from the medication chamber into the tubing, wherein the tubing extends from the syringe to the catheter and defines a tubing volume.

17. The method of claim 16, further comprising:

advancing the medication plunger a predetermined displacement to introduce a predetermined volume of medication equivalent to the tubing volume into the tubing.

18. The method of claim 16, further comprising:

engaging the retention mechanism to prevent the biasing member from advancing the medication plunger further.

* * * * *